(12) United States Patent
Yan et al.

(10) Patent No.: US 12,201,269 B2
(45) Date of Patent: Jan. 21, 2025

(54) RIGID ENDOSCOPE DEVICE

(71) Applicant: ANQING MEDICAL CO., LTD, Shanghai (CN)

(72) Inventors: Hang Yan, Shanghai (CN); Wei Tang, Shanghai (CN)

(73) Assignee: ANQING MEDICAL CO., LTD, Shanghai (CN)

( * ) Notice: Subject to any disclaimer, the term of this patent is extended or adjusted under 35 U.S.C. 154(b) by 215 days.

(21) Appl. No.: 17/431,658

(22) PCT Filed: Oct. 16, 2019

(86) PCT No.: PCT/CN2019/111377
§ 371 (c)(1),
(2) Date: Aug. 17, 2021

(87) PCT Pub. No.: WO2021/000452
PCT Pub. Date: Jan. 7, 2021

(65) Prior Publication Data
US 2022/0117473 A1   Apr. 21, 2022

(30) Foreign Application Priority Data
Jul. 4, 2019   (CN) .................... CN201910597167.3

(51) Int. Cl.
*A61B 1/04* (2006.01)
*A61B 1/00* (2006.01)
*A61B 1/06* (2006.01)

(52) U.S. Cl.
CPC ............ *A61B 1/04* (2013.01); *A61B 1/00096* (2013.01); *A61B 1/06* (2013.01)

(58) Field of Classification Search
CPC ............ A61B 1/00029; A61B 1/00066; A61B 1/00068; A61B 1/00103; A61B 1/00105;
(Continued)

(56) References Cited

U.S. PATENT DOCUMENTS

2007/0049794 A1*   3/2007   Glassenberg .......... A61B 1/042
                                                                600/179
2007/0162095 A1*   7/2007   Kimmel ............. A61B 1/00101
                                                                600/172
(Continued)

*Primary Examiner* — Aaron B Fairchild
*Assistant Examiner* — Stephen Floyd London
(74) *Attorney, Agent, or Firm* — NZ CARR LAW OFFICE

(57) ABSTRACT

A rigid endoscope device comprises a disposable endoscope body structure (2), a disposable antibacterial line mechanism (3) and a reusable camera mechanism (1). A light source (5) is provided near the front end of the endoscope body structure (2). The endoscope body structure (2) is integrated with or separated from the antibacterial line mechanism (3). The camera mechanism (1) can be linearly inserted into the endoscope body structure (2) from the rear end of the endoscope body structure (2). The antibacterial line mechanism (3) can be linearly connected to the rear end of the endoscope body structure (2) and seals at the rear end of the endoscope body structure (2), such that the camera mechanism (1) inside the endoscope body structure (2) is isolated from the outside. In the rigid endoscope device, a reusable camera mechanism (1) is isolated from the external environment and is not in contact with people, thereby effectively ensuring a sterile state thereof.

20 Claims, 5 Drawing Sheets

(58) Field of Classification Search
CPC ............ A61B 1/00114; A61B 1/00121; A61B 1/00124; A61B 1/00135; A61B 1/00137; A61B 1/00142; A61B 1/015; A61B 1/05; A61B 1/051; A61B 1/053; G03B 17/08
See application file for complete search history.

(56) References Cited

U.S. PATENT DOCUMENTS

| | | | |
|---|---|---|---|
| 2008/0108869 A1* | 5/2008 | Sanders | A61B 1/00124 600/109 |
| 2009/0082695 A1* | 3/2009 | Whitehead | A61B 1/00052 600/572 |
| 2014/0107416 A1* | 4/2014 | Birnkrant | A61B 1/00105 600/110 |
| 2014/0142383 A1* | 5/2014 | Blumenzweig | A61B 1/00057 600/110 |
| 2015/0216403 A1* | 8/2015 | Whitmore, III | A61B 1/307 600/103 |
| 2016/0198938 A1* | 7/2016 | Lizaire | A61B 1/32 600/112 |
| 2019/0246884 A1* | 8/2019 | Lu | A61B 1/018 |
| 2020/0138271 A1* | 5/2020 | Toth | A61B 1/0684 |
| 2020/0305688 A1* | 10/2020 | Sharp | A61B 1/00066 |
| 2020/0315444 A1* | 10/2020 | Ramanujam | A61B 1/00103 |
| 2021/0386411 A1* | 12/2021 | Iqbal | A61B 1/00096 |
| 2022/0240760 A1* | 8/2022 | Zhang | A61B 1/00128 |

\* cited by examiner

RIGID ENDOSCOPE DEVICE

TECHNICAL FIELD

The present invention relates to the technical field of medical instruments, and more specifically, to a rigid endoscope device.

BACKGROUND

In recent years, endoscopes and related surgical instruments have been widely used in the field of minimally invasive diagnosis and treatment. With the rapid development of minimally invasive medical technology, higher requirements have been placed on endoscopes. According to the different parts reached by the endoscope, the endoscope can be classified into neuroscope, urethral cystoscope, resectoscope, laparoscope, arthroscope, sinusoscope, laryngoscope, etc. According to the bending of the head of the endoscope, the endoscope can be divided into flexible endoscope and rigid endoscope. The endoscope device can be reusable or disposable.

The reusable endoscope device is in contact with patients, medical personnel, etc., so it needs to be sterilized and disinfected. The reusable endoscope device is not only complicated to clean and sterilize, but also has the risk of cross-infection, while the cost of the disposable endoscope device is too high.

SUMMARY

The present invention provides a rigid endoscope device to solve the problem of complicated cleaning and sterilization of the reusable endoscope, the risk of cross-infection, and the high cost of the disposable endoscope device.

According to a first aspect of the present invention, a rigid endoscope device is provided, including a disposable endoscope body structure, a disposable antibacterial line mechanism, and a reusable camera mechanism, wherein a light source is provided near a front end of the endoscope body structure; the endoscope body structure is integrated with or separated from the antibacterial line mechanism; the camera mechanism can be inserted into the endoscope body structure in a linear direction from a rear end of the endoscope body structure, and the antibacterial line mechanism can connect to and sealed at the rear end of the endoscope body structure in the linear direction, so that the camera mechanism in the endoscope body structure is isolated from the outside; the antibacterial line mechanism is configured with a disposable power cord, a power supply interface of the antibacterial line mechanism is connected with a first connection port of the camera mechanism, and a power supply of the power cord may be supplied to the first connection port through the power supply interface; the camera mechanism may be conductively connected to a light source power supply interface of the light source through a second connection port after being connected to the endoscope body structure, and a power supply of the first connection port may be supplied to the light source through the light source power supply interface and a light source wire.

Optionally, the camera mechanism includes a camera handle, a camera channel tube and a camera packaging structure; the first connection port and the second connection port are both provided at the camera handle, a camera wire connected to the camera packaging structure passes through the camera channel tube, and the power supply of the second connection port may be supplied to the camera packaging structure through the camera wire; a rear end of the camera channel tube is connected to the camera handle, and a front end of the camera channel tube is connected to the camera packaging structure; after the camera mechanism is inserted into the endoscope body structure, the camera handle, the camera channel tube and the camera packaging structure are all located in the endoscope body structure; the linear direction is a length direction of the camera channel tube.

Optionally, the endoscope body structure includes an endoscope body handle, an endoscope body channel tube and a scope hear; a rear end of the endoscope body channel tube is connected to the endoscope body handle, a front end of the endoscope body channel tube is connected to the endoscope body head, and an end of the endoscope body head is provided with a lens; after the camera mechanism is inserted into the endoscope body structure, the camera handle is located in the endoscope body handle, and the camera packaging structure is located at the endoscope body head; the endoscope body channel tube has inside a light source wire channel and a camera mechanism channel, the light source is provided at the endoscope body head, the light source wire passes through the light source wire channel, and the camera channel tube passes through the camera mechanism channel Optionally, cross-sections of the endoscope body channel tube are all crescent-shaped, the number of the light source wire channel may be separated into two groups, and the two groups of light source wire channels are symmetrically distributed on both sides of the camera mechanism channel Optionally, the endoscope body structure further includes a medium channel for gas or liquid to circulate, and a medium valve assembly communicating with the medium channel; the medium channel passes through the endoscope body channel tube and the endoscope body head in sequence, and the medium valve assembly is provided on the endoscope body handle.

Optionally, the device further includes an outer tube structure, and the outer tube structure is sleeved at an outer side of the endoscope body channel tube.

Optionally, the outer tube structure includes an outer tube channel tube, an outer tube handle, and a limit portion; the outer tube channel tube is sleeved at the outer side of the endoscope body channel tube, the outer tube handle is provided at an outer side of the outer tube channel tube, and the limit portion is provided in the outer tube channel tube for limiting a position between the outer tube channel tube and the endoscope body channel tube along a length direction thereof.

Optionally, the antibacterial line mechanism includes a sterilization line handle and a wiring interface, the power supply interface and the wiring interface are both provided at the sterilization line handle, and the power cord is connected to the sterilization line handle through the wiring interface and is connected to the power supply interface.

Optionally, if the endoscope body structure may be separated from the antibacterial line mechanism, the endoscope body structure is locked with and connected to the antibacterial line mechanism by a locking structure.

Optionally, the endoscope body structure and/or the antibacterial line mechanism is further provided with an instrument channel In the rigid endoscope device provided by the present invention, the sterility of the device is ensured by the disposable endoscope body structure and the disposable antibacterial line mechanism, which avoids the risk of sterilization and disinfection, as well as the risk of cross-infection. The present invention also avoids the waste of parts related to the camera through the reusable camera mechanism, and effectively reduces the cost. Meanwhile, the camera mechanism of the present invention may be inserted into the endoscope body structure to be isolated from the outside, avoiding the reusable camera mechanism from contacting the outside, and avoiding contact with doctors, patients, etc., thereby effectively guaranteeing the sterility.

Further, in the present invention, since the light source is arranged in the endoscope body structure, the camera mechanism may supply power to the light source after being connected, which may avoid the independent configuration of power supply devices for the light source, and may also avoid the waste of independently-configured power supply devices due to one-time use, thereby helping reduce cost. At the same time, compared with the solution in which the camera component is packaged with the light source component together, the astigmatism and reflection problem caused by the integration of the light source in the endoscope body may be avoided.

BRIEF DESCRIPTION OF THE DRAWINGS

In order to describe the embodiments of the present invention or the technical scheme in the prior art more clearly, brief introduction on drawings needed to be used in the embodiment will be made below. It is obvious that the drawings described below are merely some embodiments of the present invention, and those skilled in the technical field further can obtain other drawings according to the drawings without creative efforts.

DESCRIPTION OF REFERENCE SIGNS

1—camera mechanism;
11—first connection port;
12—second connection port;
13—camera handle;
14—camera handle;
15—camera packaging structure;
2—endoscope body structure;
21—endoscope body handle;
22—endoscope body channel tube;
221—camera mechanism channel;
222—light source wire channel;
223—medium channel;
23—gas medium valve assembly;
24—liquid medium valve assembly;
25—endoscope body head;
251—lens;
252—medium channel;
3—antibacterial line mechanism;
31—power supply interface;
32—sterilization line handle;
33—wiring interface;
34—instrument channel;
35—locking button;
4—power cord;
5—light source;
51—light source wire;
52—light source power supply interface;
6—outer tube structure;
61—outer tube channel tube;
62—outer tube handle;
63—outer tube inner channel;
64—limit portion.

DETAILED DESCRIPTION

Clear and intact description will be made on technical schemes in the embodiments of the present invention below in combination with drawings in the embodiments of the present invention. Obviously, the described embodiments are merely a part of embodiments of the present invention and are not all the embodiments. Based on the embodiments of the present invention, all the other embodiments obtained by those skilled in the art without inventive effort are within the scope of the present invention.

Terms "first", "second", "third", "fourth", and the like (if any) in the specification and claims of the present invention and the foregoing accompanying drawings are used to distinguish similar objects, but do not need to be used for describing a specific sequence or an order. It should be understood that data used in this way can be interchanged under appropriate circumstances, so that the embodiments of the present invention described herein can be implemented in an order other than those illustrated or described herein. In addition, terms "including", "having", and any variations thereof are intended to cover non-exclusive inclusions, for example, processes, methods, systems, products, or devices that contain a series of steps or units need not be limited to those clearly listed steps or units, but may include other steps or units not explicitly listed or inherent to these processes, methods, products, or devices.

The technical solutions of the present invention are described in detail below with reference to the specific embodiments. The following several embodiments may be combined with each other, and a same or similar concept or process may not be described again in some embodiments.

Figure 1:
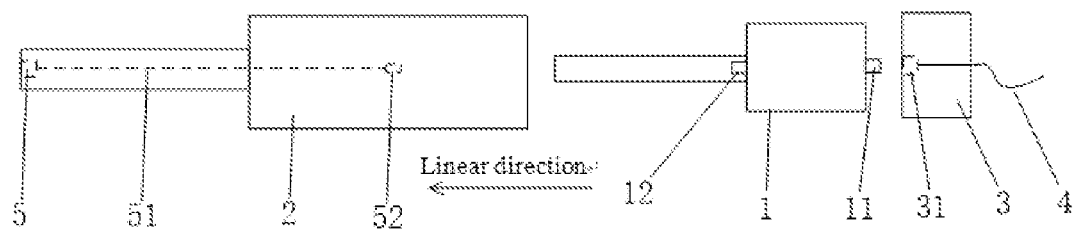
FIG. 1 is a schematic structural diagram 1 of a rigid endoscope device according to an embodiment of the present invention.
Figure 2:
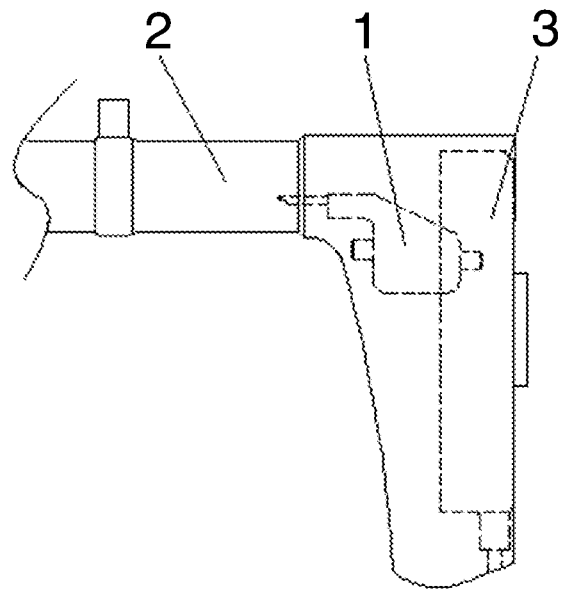
FIG. 2 is a partial schematic structural diagram of a rigid endoscope device according to an embodiment of the present invention.
Figure 3:
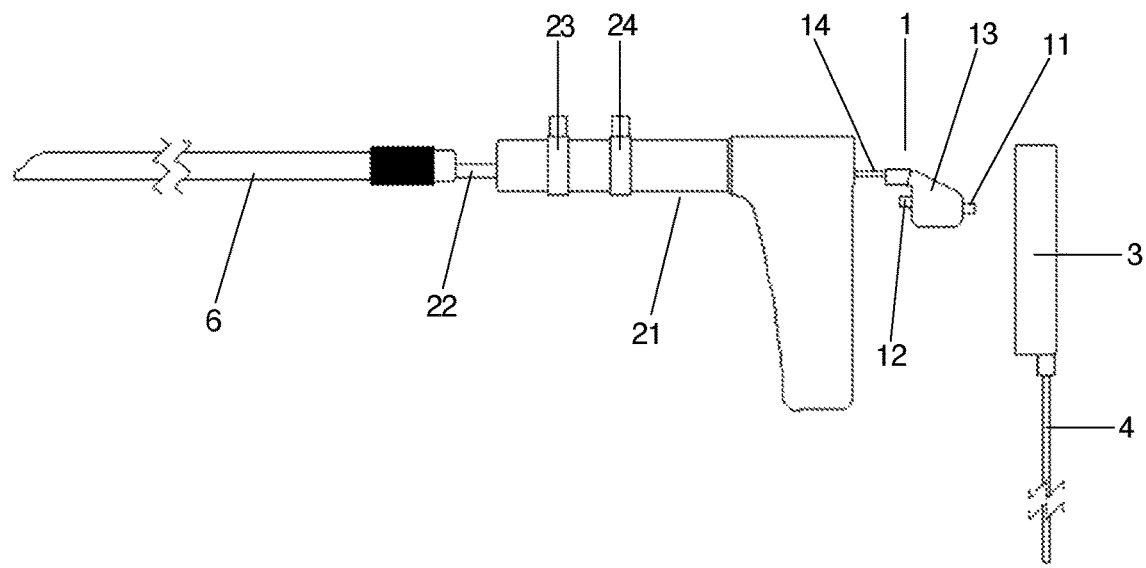
FIG. 3 is a schematic structural diagram 2 of a rigid endoscope device according to an embodiment of the present invention.

FIG. 1 is a schematic structural diagram 1 of a rigid endoscope device according to an embodiment of the present invention; FIG. 2 is a partial schematic structural diagram of a rigid endoscope device according to an embodiment of the present invention; FIG. 3 is a schematic structural diagram 2 of a rigid endoscope device according to an embodiment of the present invention.

The rigid endoscope device involved in the present embodiment may be applied to scenes such as intervertebral foramoscope, arthroscope, and hysteroscope.

With reference to FIG. 3, the rigid endoscope device includes a disposable endoscope body structure 2, a disposable antibacterial line mechanism 3, and a reusable camera mechanism 1. The endoscope body structure 2 is integrated with or separated from the antibacterial line mechanism 3.

Wherein, the camera mechanism 1 may be understood as a structure that is configured with a camera component for image acquisition and may be connected to the endoscope body structure 2.

Wherein, the endoscope body structure 2 may be understood as any structure that may accommodate the camera mechanism 1 to contact the doctor and the patient during medical activities, wherein any structure that may be sleeved outside the camera mechanism 1 may be applied to the present embodiment as the endoscope body structure 2.

Wherein the antibacterial line mechanism 3 may be understood as any structure that may isolate the camera mechanism 1 from the outside by connecting the mechanism with the endoscope body structure 2, in order to achieve a sterilization effect, and may connect the power supply of the power cord to the camera mechanism 1.

In the above embodiment, the sterility of the device is ensured by the disposable endoscope body structure and the disposable antibacterial line mechanism, which avoids the risk of sterilization and disinfection, as well as the risk of cross-infection. The above embodiment also avoids the waste of parts related to the camera through the reusable camera mechanism, and effectively reduces the cost. Wherein the camera mechanism may be reusable, is not easy to be damaged, and has low cost.

In the present embodiment, the camera mechanism 1 may be inserted into the endoscope body structure 2 in a linear direction from a rear end of the endoscope body structure 2, and the antibacterial line mechanism 3 may be connected with the rear end of the endoscope body structure 2 and sealed at the rear end of the endoscope body structure 2 in the linear direction, so that the camera mechanism 1 in the endoscope body structure 2 is isolated from the outside.

Since the present embodiment is suitable for the rigid endoscope device, the insertion of the camera mechanism 1 may be realized by linear movement in the linear direction, which may have a positive effect of facilitating assembly.

With reference to FIG. 2, an inside of the endoscope body mechanism 2 may be formed with an internal space capable of receiving the camera mechanism 1 and the antibacterial line mechanism 3, so that further, after the insertion, the camera mechanism 1 and the antibacterial line mechanism 3 are located in the internal space, thereby achieving the purpose of isolation.

In the above embodiment, the camera mechanism may be inserted into the endoscope body structure to be isolated from the outside, avoiding the reusable camera mechanism from contacting the outside, and avoiding contact with doctors, patients, etc., thereby effectively guaranteeing the sterility.

In other words, the reusable camera mechanism is completely covered, so that the parts accessible to doctors and patients are all sterilized instruments, and the non-sterile area may be completely isolated from the sterile area, which is convenient, safe and reliable to use.

In addition, the camera mechanism involved in the present embodiment may be reusable, but other related components have no camera-related components, even if they are damaged, it is not easy to cause damage to the camera-related components, which is convenient to use and very low in maintenance cost.

In the present embodiment, a light source 5 is provided near a front end of the endoscope body structure 2; the front end may be understood as an end of the endoscope body structure 2 that is used to insert into a natural cavity or incision cavity of the human scope, or as an end of the endoscope body structure 2 close to the camera component, or as an end of the endoscope body structure 2 away from the power cord and away from the handle.

The antibacterial line mechanism 3 is configured with a disposable power cord 4, a power supply interface 31 of the antibacterial line mechanism 3 is connected with a first connection port 11 of the camera mechanism 1, and a power supply of the power cord 4 may be supplied to the first connection port 11 through the power supply interface 31.

The camera mechanism 1 may be conductively connected to a light source power supply interface 52 of the light source 5 through a second connection port 12 after being connected to the endoscope body structure 2, and a power supply of the first connection port 11 may be supplied to the light source through the light source power supply interface and a light source wire. Meanwhile, the communication between the first connection port 11 of the camera component and the light source power supply interface also ensures the power supply of the camera component and the transmission of image acquisition.

In an embodiment, the first connection port 11 and the second connection port 12 may have a protruding structure, so that the power connection port may be inserted into the corresponding power supply port 31 and the light source power supply port 52. The present embodiment also does not exclude a solution in which the power supply interface 31 and the light source power supply interface 52 have the protruding structure, so as to be inserted into the first connection port 11 and the second connection port 12.

In the above embodiments, since the light source is arranged in the endoscope body structure, the camera mechanism may supply power to the light source after being connected, which may avoid the independent configuration of power supply devices for the light source, and may also avoid the waste of independently-configured power supply devices due to disposable use, thereby helping reduce cost. At the same time, compared with the solution in which the camera component is packaged with the light source component together, the astigmatism and reflection problem caused by the integration of the light source in the endoscope body may be avoided.

In addition, a channel used for the camera circuit and a channel used for the lighting circuit are not the same channel but are with physical isolation through the tube wall, so as to effectively prevent the problem of light interference.

Figure 4:
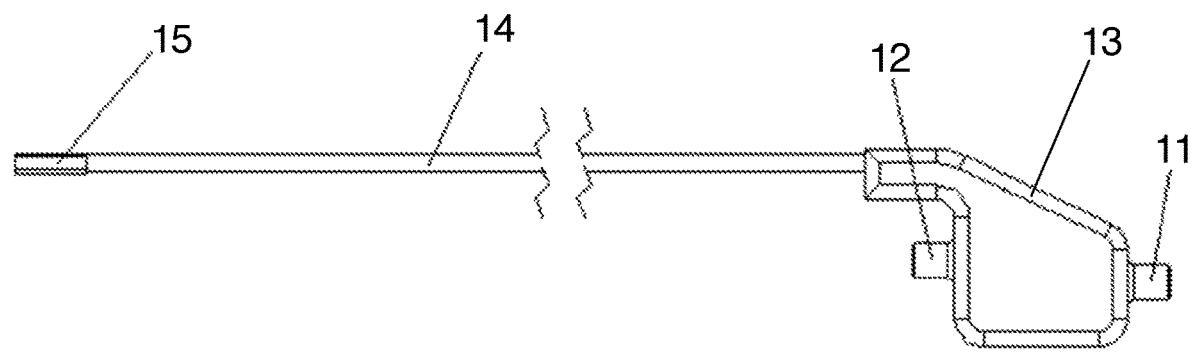
FIG. 4 is a schematic structural view of a camera mechanism according to an embodiment of the present invention.

FIG. 4 is a schematic structural view of a camera mechanism according to an embodiment of the present invention.

With reference to FIG. 4, the camera 1 includes a camera handle 13, a camera channel tube 14, and a camera packaging structure 15.

The camera packaging structure 15 may be understood as an entity having any camera components and packaged together by a packaging process to form a complete structure. Compared with the packaging structure in the related conventional art, the light source component may not be packaged in the above embodiments, and the structure in the above embodiments is relatively simplified. Further, a more compact structure may be facilitated to be made, thereby helping to achieve the effect of not increasing the outer diameter of the endoscope.

In a specific implementation process, in the camera packaging structure 15, a circuit board and a component or a combination of components for adjusting the optical path and processing electrical signals may also be configured. The camera packaging structure 15 may be connected to the camera wire via the circuit board, for example, by soldering.

The first connection port 11 and the second connection port 12 are both provided on the camera handle 13; correspondingly, in order to be suitable for the conduction between the first connection port 11 and the second connection port 12, a corresponding connection circuit may be provided inside the camera handle 13 to satisfy the requirements of power supply. At the same time, the present embodiment does not exclude that a processing circuit for processing electrical signals such as voltage and current is also configured while achieving the circuit connection. The connection circuit and the processing circuit may be arranged on the circuit board, and the connection circuit, the processing circuit and the circuit board may be arranged in the space in the camera handle 13.

A camera wire connected to the camera packaging structure 15 passes through the camera channel tube 14, and the power supply of the second connection port 11 may be supplied to the camera packaging structure 15 through the camera wire.

A rear end of the camera channel tube 14 is connected to the camera handle 13, and a front end of the camera channel tube 14 is connected to the camera packaging structure 15. The camera handle 13, the camera channel tube 14, and the camera packaging structure 15 are all located in the endoscope body structure 2 after the camera mechanism 1 is inserted into the endoscope body structure 2. In order to facilitate the camera channel tube 14 inserting into the endoscope body channel tube 22, the linear direction is a length direction of the camera channel tube 14.

The camera handle 13 may be understood as being suitable for being held by hand, so that the camera mechanism 1 may be inserted into the endoscope body structure 2 by holding the camera handle 13.

Figure 5:
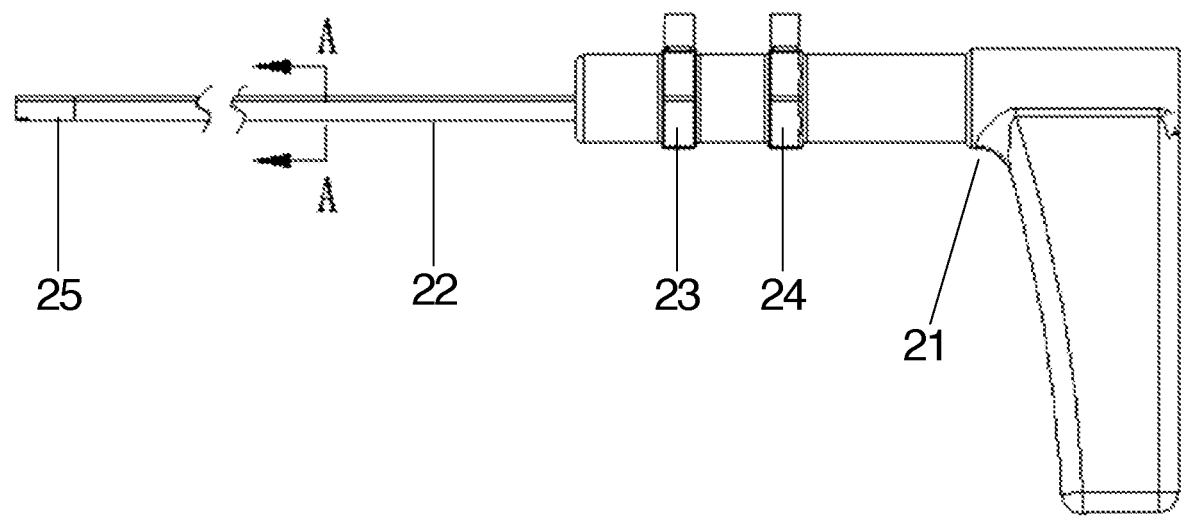
FIG. 5 is a schematic structural view of an endoscope body structure according to an embodiment of the present invention.
Figure 6:
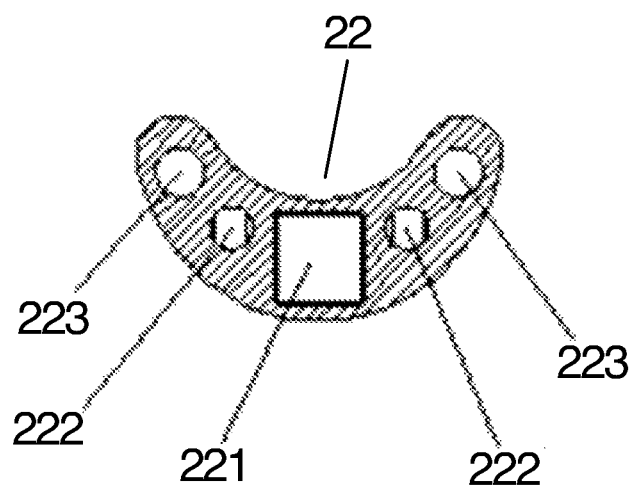
FIG. 6 is a schematic cross-sectional view of an endoscope body channel tube according to an embodiment of the present invention.
Figure 7:
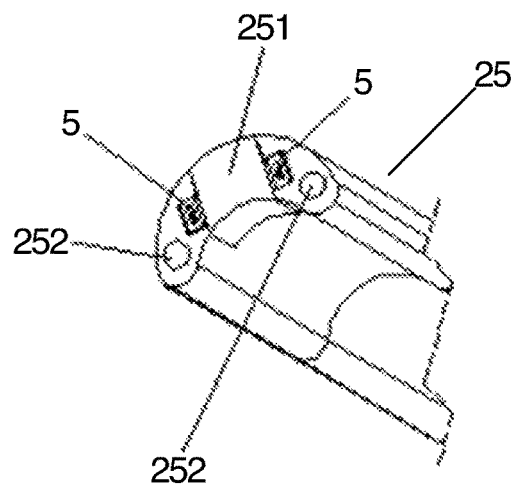
FIG. 7 is a schematic structural view of an endoscope body head according to an embodiment of the present invention.
Figure 8:
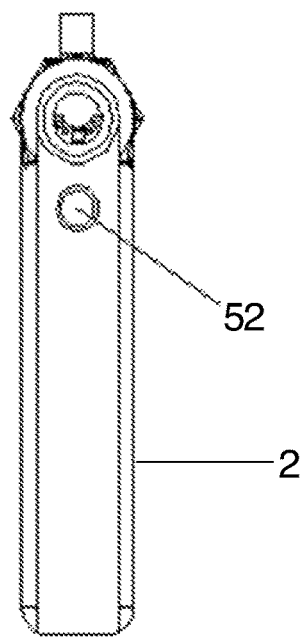
FIG. 8 is a schematic rear-end view of an endoscope body structure according to an embodiment of the present invention.

FIG. 5 is a schematic structural view of an endoscope body structure according to an embodiment of the present invention; FIG. 6 is a schematic cross-sectional view of A-A of an endoscope body channel tube according to an embodiment of the present invention; FIG. 7 is a schematic structural view of an endoscope body head according to an embodiment of the present invention; and FIG. 8 is a schematic rear-end view of an endoscope body structure according to an embodiment of the present invention.

With reference to FIGS. 5 to 8, the endoscope body structure 2 includes an endoscope body handle 21, an endoscope body channel tube 22 and an endoscope body head 25.

A rear end of the endoscope body channel tube 22 is connected to the endoscope body handle 21, and a front end of the endoscope body channel tube 22 is connected to the endoscope body head 25.

After the camera mechanism 1 is inserted into the endoscope body structure 2, the camera handle 13 is located in the endoscope body handle 21, and the camera packaging structure 15 is located at the endoscope body head 25.

With reference to FIG. 6, the endoscope body channel tube 22 has inside a light source wire channel 222 and a camera mechanism channel 221, the light source 5 is provided at the endoscope body head 25, the light source wire 51 passes through the light source wire channel 222, and the camera channel tube 14 passes through the camera mechanism channel 221.

Corresponding to the channel in the endoscope body channel tube 22, the endoscope body head 25 also has a light source receiving cavity capable of receiving the light source 5, which may be connected to the light source wire channel in the endoscope body head 25 and light source receiving cavity may be directly or indirectly connected to the light source wire channel 222, in order the light source wire to pass through.

The endoscope body head 25 may be provided with a lens 251, and the lens 251 may be a simple transparent medium that does not affect the optical path or may be a prism that forms a packaging structure that may refract the optical path so that the camera mechanism 1 may collect images in different directions of the endoscope body head. The lens 251 is arranged at the front end of the camera mechanism channel 221 and is blocked to ensure that the camera mechanism in the camera mechanism channel 221 is isolated from human tissues, doctors, and the like. In a specific implementation process, the lens 251 may be an integrated prism, which may form an observation viewing angle within a certain angle range, and the angle range may be, for example, 0 degrees to 60 degrees.

The light source wire channel 222 may be understood as a channel suitable for the light source wire 51 to pass through.

Both the camera mechanism channel 221 and the light source wire channel 222 may be understood as a linear channel along the linear direction. The cross-sectional shape of the camera mechanism channel 221 may be various, and the cross-sectional shape of the light source wire channel 222 may also be various, e.g., may be round, rectangular, trapezoidal or in other regular or irregular shapes, so as to facilitate maximizing the use of space.

In an embodiment, the cross section of the endoscope body channel tube 22 is crescent-shaped, which may be understood as having two arcs, such as a first arc and a second arc. A first end of the first arc may be directly or indirectly connected to a first end of the second arc, a second end of the first arc may be directly or indirectly connected to a second end of the second arc, and the centers of the two arcs are on the same side of the arc. The radians of the two arcs may be different, and the present embodiment does not exclude the case that the radians of the two arcs are the same.

In addition, the first end of the first arc and the first end of the second arc, and the second end of the first arc and the second end of the second arc, may be connected directly or indirectly connected through straight lines, arcs, curves, etc., with each other.

The crescent-shaped endoscope body channel tube 22 may facilitate the uniform distribution of the camera mechanism channel 221 and the light source wire channel 222. In a specific example, it can also facilitate the uniform distribution of the medium channel The number of the light source wire channel 222 may be separated into two groups, and the two groups of light source wire channels 222 are symmetrically distributed on both sides of the camera mechanism channel 221. Since the size is generally smaller than the camera mechanism channel 221, it may be matched with the crescent-shaped endoscope body channel tube 22. In a specific implementation process, the number of light source wire channels 222 in each group is one light source wire channel 222, and the present embodiment does not exclude the case where there are a plurality of light source wire channels 222 in each group.

In an embodiment, the endoscope body structure 2 further includes a medium channel for gas or liquid to circulate, and a medium valve assembly communicated with the medium channel The medium channel passes through the endoscope body channel tube and the endoscope body head in sequence, and the medium valve assembly is provided on the endoscope body handle.

The medium channel may include, for example, the medium channel 223 in the endoscope body channel tube 22 and the medium channel 252 in the endoscope body head 25, and the medium channel 223 and the medium channel 252 may be connected along the linear direction. The two medium channels 223 in the endoscope body channel tube 22 may respectively be used to circulate liquid and gas, and the two medium channels 252 in the endoscope body head 25 may respectively be used to circulate liquid and gas.

With reference to FIGS. 3 and 5, the medium valve assembly may include a gas medium valve assembly 23 and a liquid medium valve assembly 24, which respectively are communicated with a medium channel for gas circulation and a medium channel for liquid circulation.

In addition, the disposable endoscope body structure 2 may be separated from the camera mechanism 1. This situation is not simply achieved by sleeving a sheath outside the scope, so that the space may be effectively utilized, the outer diameter will not be increased, and installation and use are facilitated.

Figure 9:
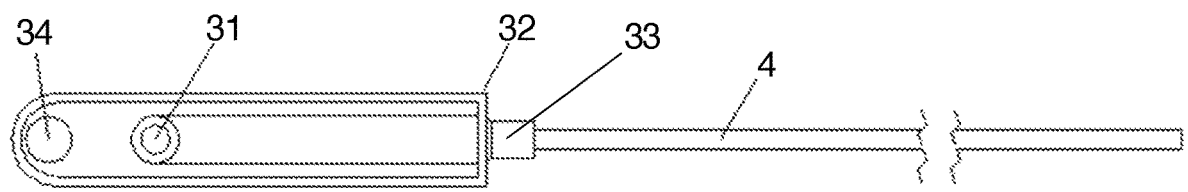
FIG. 9 is a schematic structural view of an antibacterial line mechanism according to an embodiment of the present invention.

FIG. 9 is a schematic structural view of an antibacterial line mechanism according to an embodiment of the present invention.

With reference to FIG. 9, the antibacterial line mechanism 3 includes a sterilization line handle 32 and a wiring interface 33, the power supply interface 31 and the wiring interface 33 are both provided at the sterilization line handle 32, and the power cord 4 is connected to the sterilization line handle 32 via the wiring interface 33 and is connected to the power supply interface 31.

Wherein the sterilization line handle 32 may be understood as a structure that may be adapted to be held in hand, which may have an internal space, and the power cord 4 may be connected to the power supply interface 31 after being connected to the internal space via the wiring interface 33 to achieve power supply. In a specific implementation process, the power cord 4 may be directly connected to the power supply interface 31, the power cord 4 may be indirectly connected to the power supply interface 31.

In an embodiment, the endoscope body structure 2 and/or the antibacterial line mechanism 3 is further provided with an instrument channel For example, the instrument channel 34 shown in FIG. 9.

Figure 10:
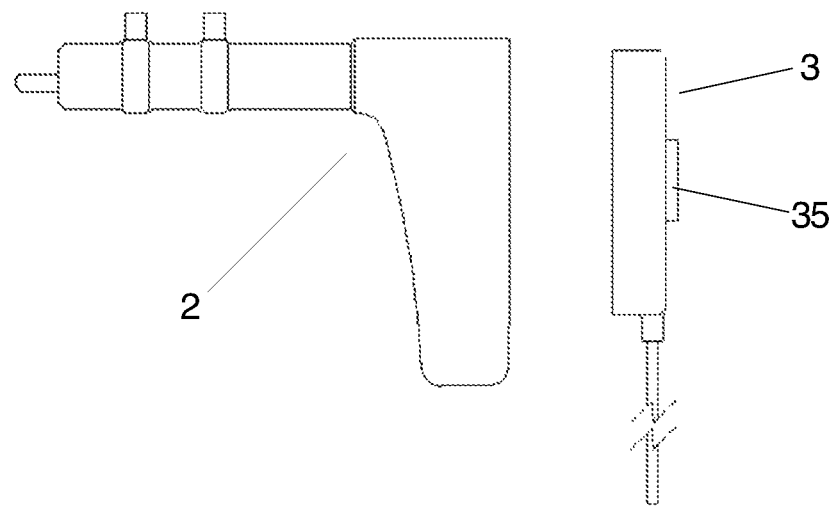
FIG. 10 is a schematic structural view of an endoscope body structure and a sterilization line according to an embodiment of the present invention.

FIG. 10 is a schematic structural view of an endoscope body structure and a sterilization line according to an embodiment of the present invention.

With reference to FIG. 10, if the endoscope body structure 2 may be separated from the antibacterial line mechanism 3, the endoscope body structure 2 may be locked with the antibacterial line mechanism 3 by a locking structure. The locking structure may be controlled by a locking button 35 for locking.

Wherein, locking structure may be understood as any structure that may realize relative locking between two parts, for example, may be a threaded structure, a latching structure, a plugging structure, and so on.

In a specific implementation process, when the locking button 35 is pressed, the sterilization line handle 32 may be pushed into the endoscope body handle 21, and then the locking button 35 may be released to achieve automatic locking, wherein if unlocking is required, the lock button 35 may pressed to unlock. It can be seen that the above embodiments may facilitate the combination and separation of the two sterilization line handles 32 and the endoscope body handle 21.

In another embodiment, the endoscope body structure 2 may also be integrated with the antibacterial line mechanism 3, wherein the antibacterial line mechanism 3 may also include a sterilization line housing and the wiring interface, the power supply interface and the wiring interface are both provided on the sterilization line handle, and the power cord is connected to the sterilization line handle through the wiring interface and is connected to the power supply interface; the sterilization line housing may be understood referring to the sterilization line handle 32 involved in the previous embodiments, and the power supply interface and the wiring interface may refer to the power supply interface 31 and the wiring interface 33 involved in the previous embodiments.

In a specific implementation process, a plug-in interface may be formed between the endoscope body structure 2 and the antibacterial line mechanism 3. After the camera mechanism is plugged in, it may be clamped to be fixed in position, and after plug-in, it may be directly or indirectly conducted through the interface for meeting the aforementioned conduction requirements.

It can be seen that the above antibacterial line mechanism is configured with sterilization line handles and corresponding interfaces, which may completely isolate the bacteria area and solve the inconvenience caused by interfaces such as sterilization sheaths.

Figure 11:
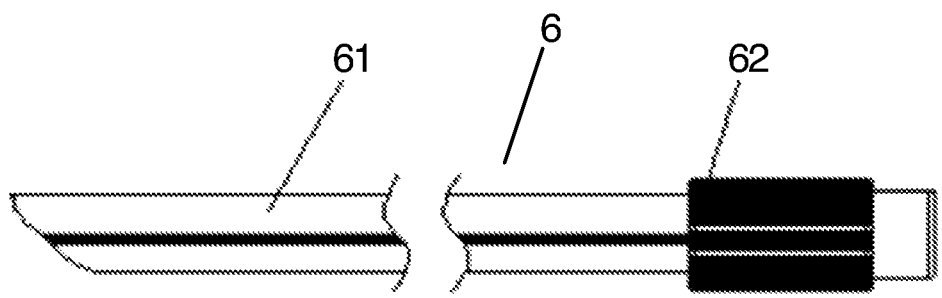
FIG. 11 is a schematic structural view of an outer tube structure according to an embodiment of the present invention.
Figure 12:
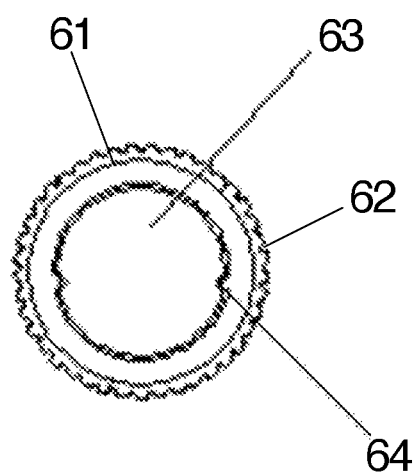
FIG. 12 is a schematic end-surface view of an outer tube structure according to an embodiment of the present invention.

FIG. 11 is a schematic structural view of an outer tube structure according to an embodiment of the present invention; FIG. 12 is a schematic end-surface view of an outer tube structure according to an embodiment of the present invention.

With reference to FIGS. 11 and 12, the device further includes an outer tube structure 6, and the outer tube structure 6 is sleeved at an outer side of the endoscope body channel tube 22. The outer tube structure 6 may provide a working channel for the instrument and/or the endoscope body channel tube 22 while serving as a support.

In an embodiment, the outer tube structure 6 includes an outer tube channel tube 61, an outer tube handle 62, and a limit portion 64; the outer tube channel tube 61 is sleeved at the outer side of the endoscope body channel tube, the outer tube handle 62 is provided at an outer side of the outer tube channel tube 61, and the limit portion 64 is provided in the outer tube channel tube 61 for limiting a position between the outer tube channel tube 61 and the endoscope body channel tube 22 along a length direction thereof. The outer tube channel tube 61 may be formed with an outer tube inner channel 63 that may allow the endoscope body channel tube 22 and/or instruments to pass through.

In a specific implementation process, the limit portion 64 may be provided at a position close to the front end of the outer tube channel tube 61, so as to prevent the endoscope body channel tube 22 from passing through the outer tube channel tube 61. It can be seen that the endoscope body channel tube 22 may be fixed with respect to the outer tube structure 6 through the limit portion 64.

Moreover, the cross section of the outer tube channel tube 61 of the outer tube structure 6 may be circular or elliptical, or any other irregular shape, so as to change the size of the instrument channel, adapt to more surgical needs, and at the same time to maximize the use of space. Further, since the outer tube structure 6 is independently manufactured, an elliptical structure may also be designed, which is beneficial to increase the size of the channel In summary, in the rigid endoscope device provided by the present embodiment, the sterilization of the device is ensured by the disposable endoscope body structure and the disposable antibacterial line mechanism, which avoids the risk of sterilization and disinfection, as well as the risk of cross-infection. The present embodiment also avoids the waste of parts related to the camera by using the reusable camera mechanism, and effectively reduces the cost. Meanwhile, the camera mechanism of the present embodiment may be inserted into the endoscope body structure to be isolated from the outside, avoiding the reusable camera mechanism contacting from the outside, and avoiding contact with doctors, patients, etc., thereby effectively guaranteeing the sterilization.

Furthermore, in the present embodiment, since the light source is arranged in the endoscope body structure, the camera mechanism may supply power to the light source after being connected, which may avoid the independent configuration of power supply devices for the light source, and may also avoid the waste of independently-configured power supply devices due to one-time use, thereby helping reduce cost. At the same time, the astigmatism and reflection problem caused by the integration of the light source in the endoscope body may be avoided, compared with the solution in which the camera component is packaged with the light source component together.

At last, it should be noted that the above various embodiments are only used to describe the technical solutions of the present invention, rather than limiting the technical solutions of the present invention. Even though the present invention is described in detail with reference to the foregoing embodiments, those skilled in the art should understand that they can still modify the technical solutions recorded in the foregoing various embodiments or equivalently replace some or all of the technical features. However, these modifications or replacements do not make the essence of the corresponding technical solutions deviate from the scope of the technical solutions of the embodiments of the present invention.

What is claimed is:

1. A rigid endoscope device, comprising a disposable endoscope body structure, a disposable antibacterial line mechanism, and a reusable camera mechanism,
   wherein a light source is provided near a front end of the endoscope body structure;
   the endoscope body structure is integrated with or separated from the antibacterial line mechanism, the endoscope body structure comprises an endoscope body channel tube having a camera mechanism channel therein; the camera mechanism comprises a camera handle, a camera channel tube and a camera packaging structure, the camera handle is suitable for being held by hand so that the camera mechanism is removably inserted into the camera mechanism channel of the endoscope body structure in a linear direction from a rear end of the endoscope body structure, and the antibacterial line mechanism is operable to be connected with the rear end of the endoscope body structure in the linear direction and sealed at the rear end of the endoscope body structure, such that the camera mechanism inside the endoscope body structure is isolated from the outside;
   the antibacterial line mechanism comprises a disposable power cord, a power supply interface of the antibacterial line mechanism is connected with a first connection port of the camera mechanism, and a power supply of the power cord is supplied to the first connection port via the power supply interface;
   the camera mechanism is operable to be connected to a light source power supply interface of the light source through a second connection port after being connected to the endoscope body structure, and a power supply of the first connection port is supplied to the light source through the light source power supply interface and a light source wire.

2. The device according to claim 1, wherein
   the first connection port and the second connection port are both provided at the camera handle, a camera wire connected to the camera packaging structure passes through the camera channel tube, and a power supply of the second connection port is supplied to the camera packaging structure through the camera wire;
   a rear end of the camera channel tube is connected to the camera handle, and a front end of the camera channel tube is connected to the camera packaging structure;
   after the camera mechanism is inserted into the endoscope body structure, the camera handle, the camera channel tube and the camera packaging structure are all located in the endoscope body structure;
   the linear direction is a length direction of the camera channel tube.

3. The device according to claim 2, wherein the endoscope body structure comprises an endoscope body handle, the endoscope body channel tube and an endoscope body head; a rear end of the endoscope body channel tube is connected to the endoscope body handle, a front end of the endoscope body channel tube is connected to the endoscope body head, and a rear end of the endoscope body head is provided with a lens;
   after the camera mechanism is inserted into the endoscope body structure, the camera handle is located in the endoscope body handle, and the camera packaging structure is located at the endoscope body head;
   the endoscope body channel tube has a light source wire channel therein, the light source is provided at the endoscope body head, the light source wire passes through the light source wire channel, and the camera channel tube passes through the camera mechanism channel.

4. The device according to claim 3, wherein cross-sections of the endoscope body channel tube are all crescent-shaped, the number of the light source wire channel is separated into two groups, and the two groups of light source wire channels are symmetrically distributed on both sides of the camera mechanism channel.

5. The device according to claim 3, wherein the endoscope body structure further comprises a medium channel for gas or liquid to circulate, and a medium valve assembly communicating with the medium channel; the medium channel passes through the endoscope body channel tube and the endoscope body head in sequence, and the medium valve assembly is provided on the endoscope body handle.

6. The device according to claim 3, further comprising an outer tube structure, the outer tube structure is sleeved at an outer side of the endoscope body channel tube.

7. The device according to claim 6, wherein the outer tube structure comprises an outer tube channel tube, an outer tube handle, and a limit portion; the outer tube channel tube is sleeved at the outer side of the endoscope body channel tube, the outer tube handle is provided at an outer side of the outer tube channel tube, and the limit portion is provided in the outer tube channel tube for limiting a position between the outer tube channel tube and the endoscope body channel tube along a length direction thereof.

8. The device according to claim 1, wherein the antibacterial line mechanism comprises a sterilization line handle and a wiring interface, the power supply interface of the antibacterial line mechanism and the wiring interface are both provided at the sterilization line handle, and the power cord is connected to the sterilization line handle through the wiring interface and is connected to the power supply interface of the antibacterial line mechanism.

9. The device according to claim 1, wherein if the endoscope body structure is separable from the antibacterial line mechanism, the endoscope body structure is locked with the antibacterial line mechanism by a locking structure.

10. The device according to claim 1, wherein the endoscope body structure and/or the antibacterial line mechanism is further provided with an instrument channel.

11. The device according to claim 4, wherein the endoscope body structure further comprises a medium channel for gas or liquid to circulate, and a medium valve assembly communicating with the medium channel; the medium channel passes through the endoscope body channel tube and the endoscope body head in sequence, and the medium valve assembly is provided on the endoscope body handle.

12. The device according to claim 4, further comprising an outer tube structure, the outer tube structure is sleeved at an outer side of the endoscope body channel tube.

13. The device according to claim 2, wherein the antibacterial line mechanism comprises a sterilization line handle and a wiring interface, the power supply interface of the antibacterial line mechanism and the wiring interface are both provided at the sterilization line handle, and the power cord is connected to the sterilization line handle through the wiring interface and is connected to the power supply interface of the antibacterial line mechanism.

14. The device according to claim 3, wherein the antibacterial line mechanism comprises a sterilization line handle and a wiring interface, the power supply interface of the antibacterial line mechanism and the wiring interface are both provided at the sterilization line handle, and the power cord is connected to the sterilization line handle through the wiring interface and is connected to the power supply interface of the antibacterial line mechanism.

15. The device according to claim 4, wherein the antibacterial line mechanism comprises a sterilization line handle and a wiring interface, the power supply interface of the antibacterial line mechanism and the wiring interface are both provided at the sterilization line handle, and the power cord is connected to the sterilization line handle through the wiring interface and is connected to the power supply interface of the antibacterial line mechanism.

16. The device according to claim 2, wherein if the endoscope body structure is separable from the antibacterial line mechanism, the endoscope body structure is locked with the antibacterial line mechanism by a locking structure.

17. The device according to claim 3, wherein if the endoscope body structure is separable from the antibacterial line mechanism, the endoscope body structure is locked with the antibacterial line mechanism by a locking structure.

18. The device according to claim 4, wherein if the endoscope body structure is separable from the antibacterial line mechanism, the endoscope body structure is locked with the antibacterial line mechanism by a locking structure.

19. The device according to claim 2, wherein the endoscope body structure and/or the antibacterial line mechanism is further provided with an instrument channel.

20. The device according to claim 3, wherein the endoscope body structure and/or the antibacterial line mechanism is further provided with an instrument channel.

* * * * *